United States Patent
Sensinger et al.

(10) Patent No.: US 11,246,721 B2
(45) Date of Patent: Feb. 15, 2022

(54) LOCKABLE FINGER SYSTEM AND RELATED METHODS

(71) Applicant: Rehabilitation Institute of Chicago, Chicago, IL (US)

(72) Inventors: Jon Sensinger, Fredericton (CA); Ashley Swartz, Chicago, IL (US); James H. Lipsey, Oak Park, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 16/657,638

(22) Filed: Oct. 18, 2019

(65) Prior Publication Data

US 2020/0054464 A1 Feb. 20, 2020

Related U.S. Application Data

(62) Division of application No. 15/185,873, filed on Jun. 17, 2016, now abandoned.

(60) Provisional application No. 62/182,253, filed on Jun. 19, 2015.

(51) Int. Cl.
*A61F 2/58* (2006.01)
*A61F 2/50* (2006.01)

(52) U.S. Cl.
CPC .............. *A61F 2/586* (2013.01); *A61F 2/583* (2013.01); *A61F 2002/5072* (2013.01); *A61F 2002/587* (2013.01)

(58) Field of Classification Search
CPC ...................................................... A61F 2/586
See application file for complete search history.

(56) References Cited

U.S. PATENT DOCUMENTS

| | | | | |
|---|---|---|---|---|
| 1,277,747 A | * | 9/1918 | O'Connor | A61F 2/54 623/63 |
| 1,484,913 A | * | 2/1924 | Surry | A61F 2/583 623/63 |
| 2,493,776 A | * | 1/1950 | Pecorella | A61F 2/583 623/64 |
| 4,114,464 A | * | 9/1978 | Schubert | B25J 15/0213 74/89.14 |
| 5,219,366 A | * | 6/1993 | Scribner | A61F 2/583 623/57 |
| 5,800,571 A | * | 9/1998 | Carlson | A61F 2/68 623/57 |

(Continued)

*Primary Examiner* — Jacqueline Woznicki
(74) *Attorney, Agent, or Firm* — Polsinelli PC

(57) ABSTRACT

A prosthetic device having a proximal interphalangeal joint (PIP) and a metacarpophalangeal joint (MCP), comprising a first prosthetic digit comprising one or more first phalanges and a four-bar linkage to operatively couple the PIP joint to the MCP joint, a first engagement portion positioned on one of the first phalanges, the first engagement portion comprising a locking linkage extending along the phalange, the locking linkage being part of the four-bar linkage, and a first stopping portion comprising a stopping element configured to be positioned above the locking linkage, wherein the locking linkage is capable of engaging with the stopping element by passing the one of the first phalanges in which the locking linkage is positioned through a mechanical singularity to lock the first prosthetic digit such that each of the one or more phalanges is in a position of flexion in response to a force applied to the first prosthetic digit.

6 Claims, 14 Drawing Sheets

(56) References Cited

U.S. PATENT DOCUMENTS

| | | | |
|---|---|---|---|
| 5,941,914 A * | 8/1999 | Jacobsen | A61F 2/586 623/64 |
| 2003/0195638 A1* | 10/2003 | Kajitani | A61F 2/72 623/64 |
| 2005/0021154 A1* | 1/2005 | Brimalm | A61F 2/586 623/64 |
| 2008/0109084 A1* | 5/2008 | Maitland | A61F 2/586 623/21.15 |
| 2008/0133019 A1* | 6/2008 | Andrysek | A61F 2/68 623/20.14 |
| 2010/0036507 A1* | 2/2010 | Gow | A61F 2/583 623/64 |
| 2013/0035771 A1* | 2/2013 | Pedersen | A61F 2/586 623/65 |
| 2013/0053984 A1* | 2/2013 | Hunter | A61F 2/586 623/64 |
| 2013/0175816 A1* | 7/2013 | Kawasaki | B25J 15/0028 294/198 |
| 2014/0081425 A1* | 3/2014 | Sensinger | A61F 2/586 623/64 |
| 2015/0230941 A1* | 8/2015 | Jury | A61F 2/586 623/64 |
| 2017/0007424 A1* | 1/2017 | Gill | G06F 3/0416 |
| 2017/0020691 A1* | 1/2017 | Thompson, Jr. | A61F 2/586 |
| 2019/0328550 A1* | 10/2019 | Akhtar | A61F 2/586 |
| 2020/0306059 A1* | 10/2020 | Cornman | A61F 2/68 |
| 2021/0085490 A1* | 3/2021 | Griebling | A61F 2/586 |
| 2021/0085491 A1* | 3/2021 | Akhtar | A61F 2/586 |

* cited by examiner

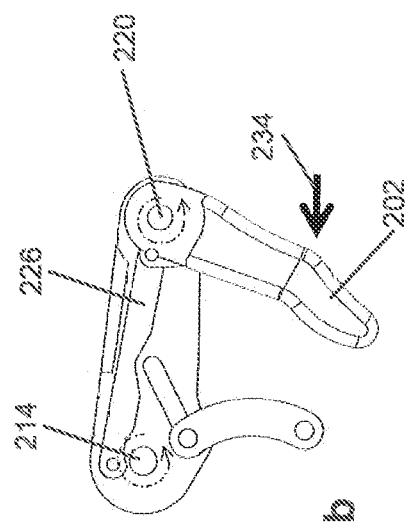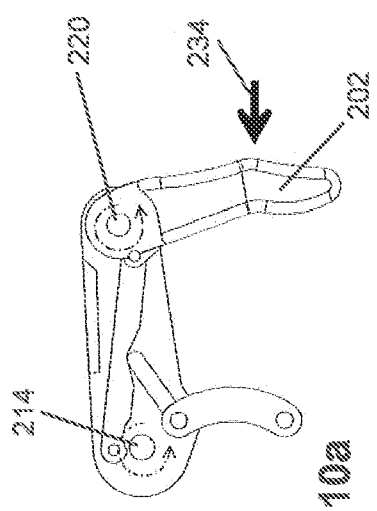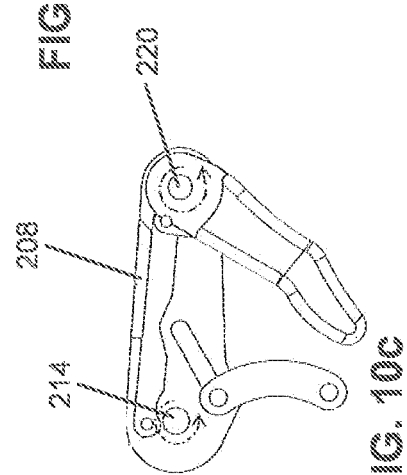

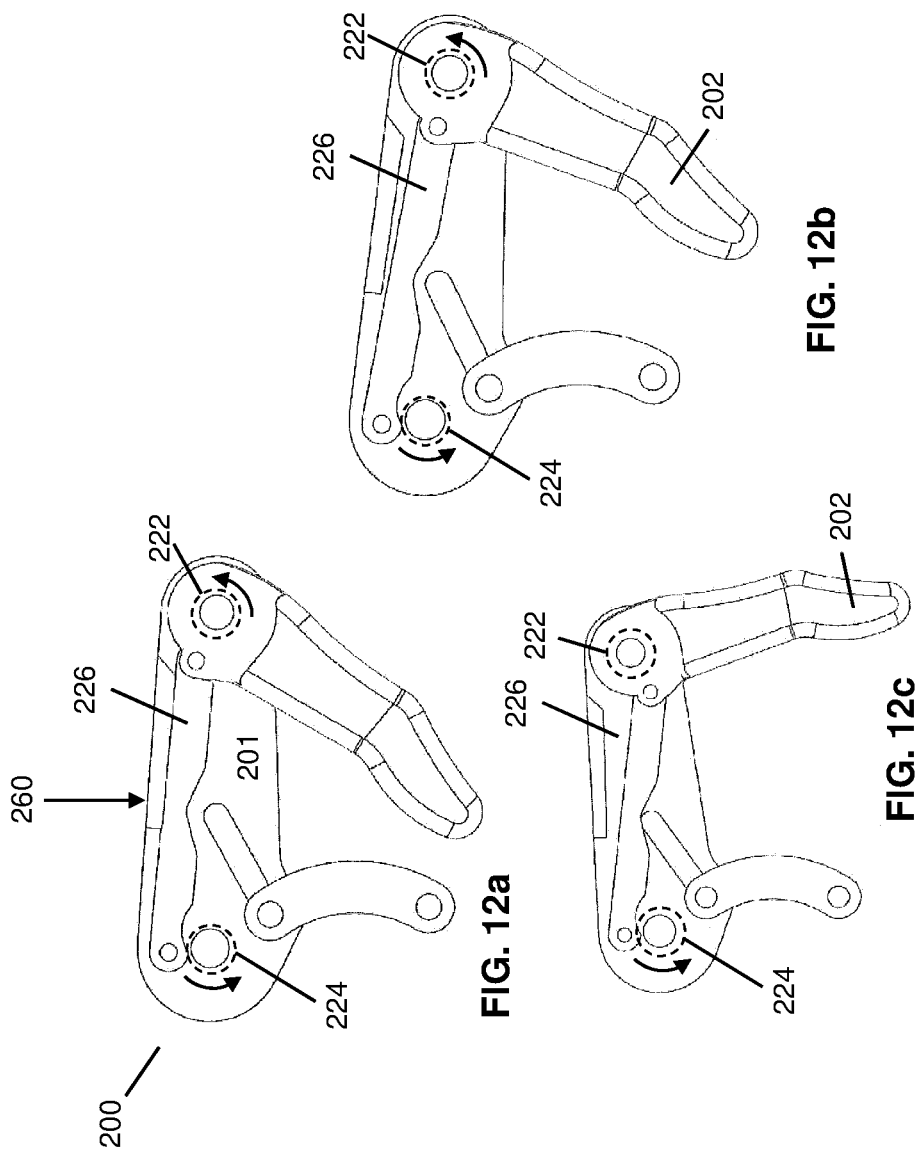

LOCKABLE FINGER SYSTEM AND RELATED METHODS

RELATED APPLICATIONS

This application is a divisional of and claims priority to U.S. Non-Provisional patent application Ser. No. 15/185,873, filed on Jun. 17, 2016, entitled "Lockable Finger System and Related Methods", which, in turn, claims priority to U.S. Provisional Patent Application No. 62/182,253, filed on Jun. 19, 2015, also entitled "Lockable Finger System and Related Methods." The entireties of U.S. Non-Provisional Patent Application No. 15/185,873 and U.S. Provisional Patent Application No. 62/182,253 are incorporated herein by reference.

FEDERALLY SPONSORED RESEARCH OR DEVELOPMENT

This invention was made with government support under H133G120059awarded by the National Institute for Disability and Rehabilitation Research (NIDRR). The government has certain rights in the invention.

TECHNICAL FIELD

The application relates generally to prosthetic devices and in particular, to a lockable finger for a prosthesis.

BACKGROUND

An estimated 41,000 people in the United States have lost use of one or both of their upper limbs through amputation at or above wrist level. See K. Ziegler-Graham, et al., "Estimating the prevalence of limb loss in the United States: 2005 to 2050," *Archives of Physical Medicine and Rehabilitation*, vol. 89, pp. 422-429, Mar 2008. Loss of the arm and hand profoundly limits everyday activities such as dressing and eating, affects social interactions and personal relationships, and can threaten basic independence. In particular, difficulty in grasping and holding objects impedes leisure activities and may prevent a return to employment. The most effective treatment for limb loss is replacement of the missing limb with a prosthetic device. Most upper limb amputations are caused by trauma and occur in relatively young, active individuals, who need prostheses that effectively replace functional dexterity of the lost hand.

Prosthetic devices for individuals with upper limb loss include myoelectric devices (which are controlled by electromyographic (EMG) signals from muscle) and body-powered prostheses (in which movement of a remaining joint, e.g., shoulder flexion, is physically coupled to the prosthetic joint through a harness and Bowden cabling system). A Bowden cabling system, in general, is a flexible cable system which transfers a mechanical force and operates inside a hollow tube. In prosthetics, Bowden cabling systems are used to operate a body-powered device. For example, the user wears a harness across his or her shoulders. The Bowden cable attaches at one end to the harness and the opposite end attaches to the prosthesis (hand or hook or some other device used to manipulate objects in the user's environment). The user then moves his or her shoulders (typically scapular retraction/protraction) to create tension in the cable which results in movement in the terminal device. A Bowden cable can be useful for this application because the hollow tube surrounding the moving cable protects the user's skin from the friction of the moving cable.

The terminal device of a prosthesis is the means by which a user directly interacts with and manipulates their environment. It is the device worn at the end of the prosthesis used to interact with the surrounding environment, and often is considered part of a prosthesis. Examples of terminal devices includes hooks and hands. Terminal devices may alternatively take on many unique and specialized shapes. For example, there are several different special terminal devices for playing sports such as baseball or golf. Thus, the functional utility of the terminal device often plays a role in determining the user's overall ability to perform necessary or desired activities.

The human hand is a highly complex mechanism with many joints. The MCP joint is the "Metacarpophalangeal joint"—these joints are what we commonly refer to as our knuckles. The PIP joint is the "proximal interphalangeal joint"—these are the joints we think of when we think of bending our fingers, the middle joint between the knuckles and the small joint at the finger tips. There are different classifications of common grasps that the hand uses when performing activities of daily living. One distinction is the difference between power and precision grasps. One study has shown that daily usage of these two types of grasps is fairly equal. See J. Z. Zheng, et al., "An investigation of grasp type and frequency in daily household and machine shop tasks," presented at the IEEE International Conference on Robotics and Automation, 2011. Examples of functional hand grasps include 3-jaw chuck, fine-pinch, trigger, and cylindrical grasps. Examples of precision grapes include fine pinch, trigger, and 3-jaw chuck. Examples of power grasps include cylindrical grasp and "power" grasp (like a fist). Users of prosthetics can use power grasps, for example, for tasks like holding heavy objects, holding drinking glasses, or positioning a jar to open.

Most myoelectric prostheses are electrically powered by batteries and rely on limit switches, potentiometers, force sensitive resistors, or myoelectric sensors for control inputs. Currently available myoelectrically controlled hands are cosmetically appealing and can apply high pinch force, but are quite heavy, are not robust, and are very expensive. Recent myoelectric hands such as the iLimb ultra (Touch Bionics) and the Bebionic 3 hand (SteeperUSA) have achieved a variety of grasps by powering each finger in the hand. These hands can accomplish several grasps, including power grip, key grip, 3-jaw-chuck, and fine pinch; however, in order to accomplish these grasps multiple actuators are required to control each finger individually, which adds weight to the hand and increases its size.

Body-powered terminal devices include prehensors (e.g., split-hooks and other non-anthropomorphically shaped terminal devices) and hands. Body-powered prehensors and hands are available in one of two modes. Voluntary open (VO) devices are opened by actuation of the Bowden cable and have a default closed position, whereas voluntary close (VC) devices have a default open position and are closed by actuation of the Bowden cable. Both VO and VC devices provide advantages and disadvantages to the user, depending on the task at hand.

In general, body-powered prehensors are considered more functional than body-powered hands. See C. M. Fryer, et al., "Body-Powered Components," in *Atlas of Amputations and Limb Deficiencies*, D. G. Smith, et al., Eds., 3rd ed Rosemont, IL: American Academy of Orthopaedic Surgeons, 2004, pp. 131-143 (hereinafter, "Fryer"). Body-powered hands often do not look natural, and functionally they can be slow, heavy, and awkward, and provide a weak grip force. They do not open very wide, and the user must expend a lot of energy to operate them.

Both VO and VC hands are commercially available—such as the APRL VC hand; the Becker Lock-Grip hand, and the Sierra VO hand. However, VO hands are seldom used due to their poor pinch forces (as explained in the Fryer reference) and the relaxed position of the VC hands is an open grasp, which is not cosmetically appealing. In addition, these body-powered prosthetic hands are very bulky in the palm section, which further impacts cosmesis. The added weight of a cosmetic shell makes the weight of body-powered hands (300-450 g) heavier than certain prehensors (113-354 g), and similar to certain myoelectric hands (250-440 g). Finally, during pinch grips, substantial user force can be lost due to deformation of the cosmetic glove. These functional and cosmetic issues together result in low user-acceptance rates for available body-powered hands (see Fryer).

Currently available body-powered hands provide a single degree of movement, actuated through a Bowden cable that drives all of the fingers together. In some devices, movement of the thumb is coupled to movement of the fingers, in others the fourth and fifth fingers remain stationary, or their linkages are compliant, for example they are made of a compliant rubber or are biased by a spring, rather than being rigid (such as hard plastic is rigid). In all cases, only a single grasp can be obtained.

Body-powered fingers typically have a single axis of rotation, located at the metacarpophalangeal (MCP) joint. Such a design requires a pre-flexed proximal interphalangeal (PIP) joint, which does not result in a cosmetically appealing palm-flat posture.

However, it is important to note that many grasps may be described as a static posture with movement of a subset of fingers. For example, in cylindrical grip, all of the fingers move together. In three-jaw chuck grip, the fourth and fifth digits are fully flexed, and only the second and third digits move. In trigger-grip, the third, fourth, and fifth digits are fully flexed, and only the second digit moves.

Fine manipulation tasks usually involve the first finger and thumb, or the first finger, second finger, and thumb. The three-jaw-chuck grip (which uses the thumb, middle, and index fingers) provided by existing prostheses serves as a compromise between power and precision grasps. The fourth and fifth fingers do not contribute functionally to fine manipulation; they are present principally for cosmesis in most available hands, and secondarily used for object stabilization. In body-powered devices, they do not transmit force from the Bowden cable to objects, but they often get in the way of many precision grasps, as the palm and fingers of the hand are typically positioned in the user's line of sight to the object being grasped. This can prevent visual feedback, unless the user adopts an unnatural posture.

Thus a grasping device that is able to maintain a static posture while select digits are actuated could achieve a substantial subset of important grasps, without the need for multiple actuators. In addition, a prosthetic grasping device only requires actuation for digit flexion—it is not necessary to actuate digit extension, which can be achieved passively using springs.

SUMMARY

In one embodiment, a prosthetic device may comprise a prosthetic digit, an engagement portion, and a stopping portion. The engagement portion is capable of engaging with the stopping portion to lock the prosthetic digit in a position of flexion in response to a force applied to the prosthetic digit.

DESCRIPTION OF THE FIGURES

FIGS. 10a, 10b, and 10c show side view stages of the lockable finger shown in FIG. 9 as it is locked in a position of flexion.

FIGS. 12a, 12b, and 12c show side views of the lockable finger shown in FIG. 9 as it is being unlocked.

DETAILED DESCRIPTION

Figure 1:
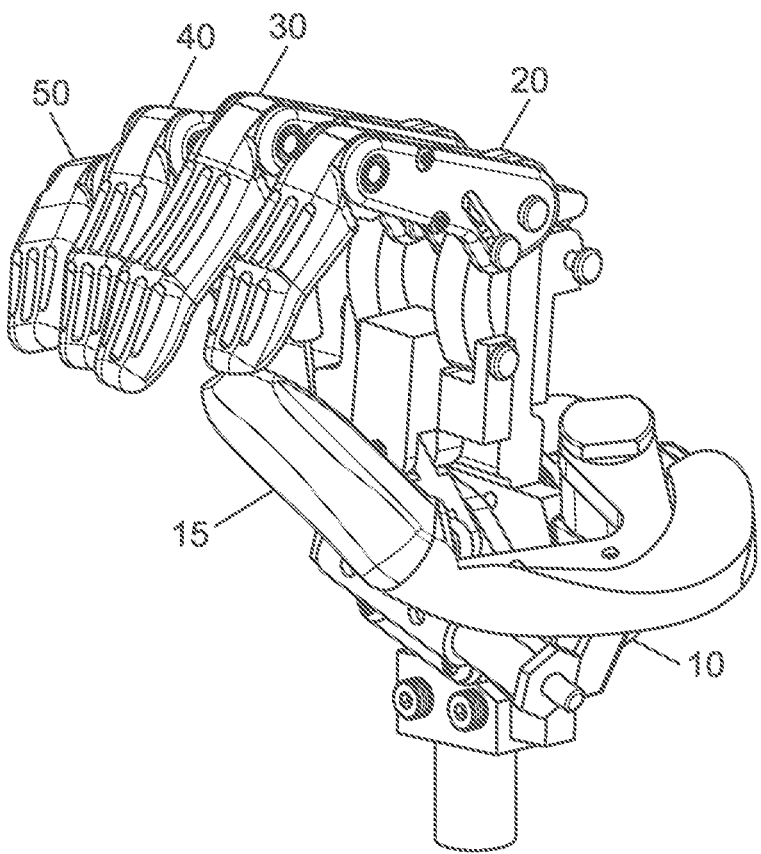
FIG. 1 shows a perspective view of a prosthetic hand arranged in a "fine pinch" position.

The locking aspects of the embodiments described here may be utilized in a variety of prostheses. Examples include those described in U.S. patent application Ser. Nos. 14/030,095, 14/614,187, 14/614,231, and 14/614,256, all of which are incorporated by reference.

Referring to the drawings, embodiments of the device are illustrated and indicated numerically in the accompanying figures.

FIG. 1 shows a view of a prosthetic hand 10 having a thumb 15, an index finger 20, a middle finger 30, a ring finger 40, and a pinky finger 50. The hand 10 is arranged in a position known as "fine pinch," where the index finger 20 and the thumb 15 pinch together in an effort to grasp a relatively small object, such as a pen. As shown in FIG. 1, the middle finger 30, the ring finger 40, and the pinky finger 50 are not used to grasp the object. In certain situations, fingers 30, 40, and 50 can even get in the way of the user's attempt to use the "fine pinch" grasp to pick up the object. For instance, they can block the view of the object from the user, or physically interfere with the object.

Figure 2:
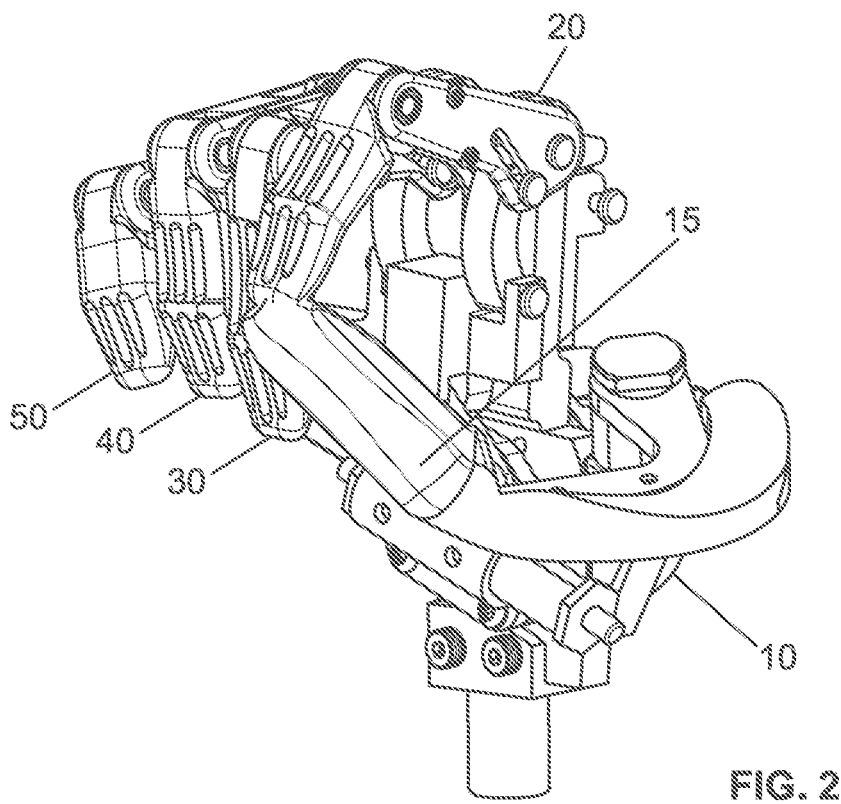
FIG. 2 shows a perspective view of a prosthetic hand arranged in a "fine pinch" position with the middle finger, ring finger, and pinky finger locked in a position of flexion.

FIG. 2 shows a view of the same prosthetic hand 10, but with fingers 30, 40, and 50 each locked in a position of flexion. Locking the fingers 30, 40, and 50 when the hand is in the fine pinch position allows the user to more accurately grasp the pen or other object, including helping the user see the object he or she is trying to grasp.

Figure 3:
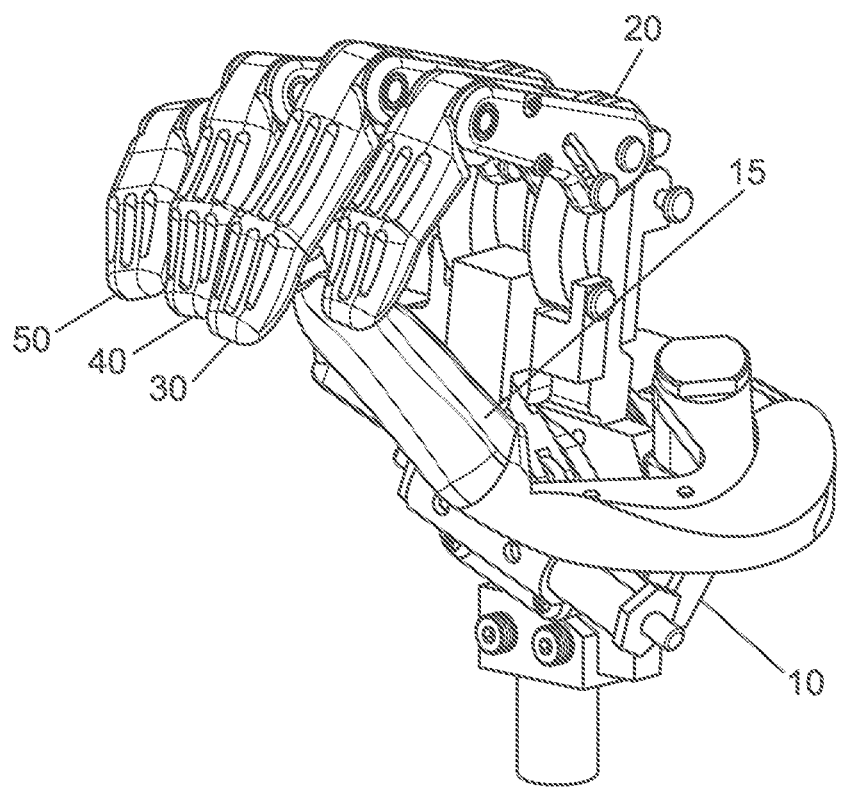
FIG. 3 shows a perspective view of a prosthetic hand arranged in a "three-jaw-chuck" position.
Figure 4:
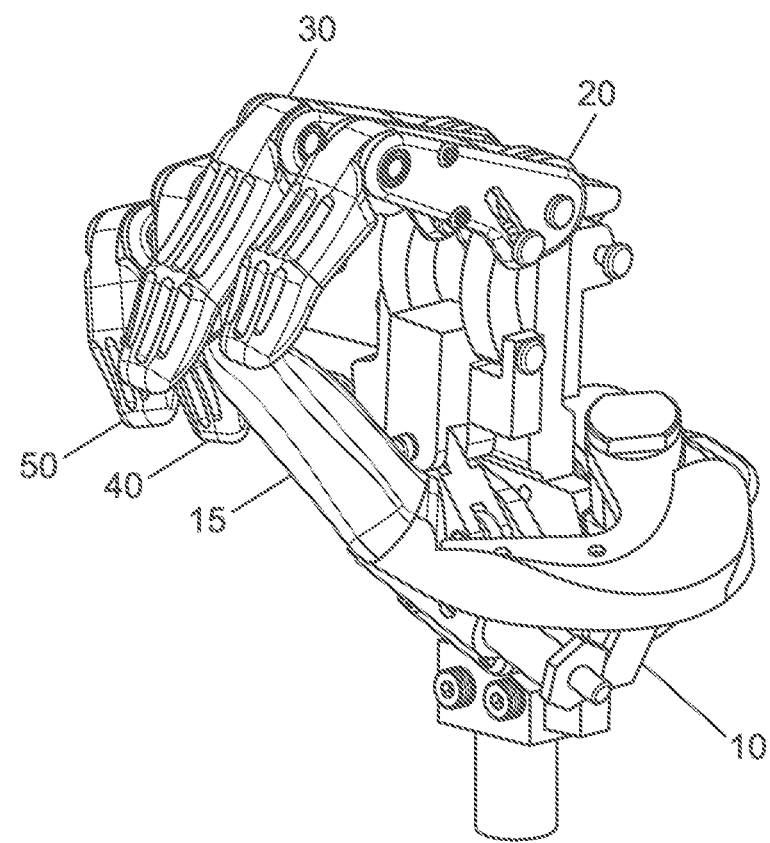
FIG. 4 shows a perspective view of a prosthetic hand arranged in a "three-jaw-chuck" position with the ring finger and the pinky finger locked in a position of flexion.

FIGS. 3 and 4 show the hand 10 in a "three-jaw-chuck" position, where both the index finger 20 and the middle finger 30 pinch together with the thumb 15. A user may use the three-jaw-chuck position, for instance, when the user wants to grasp an item like a pen or silverware, which requires precision but some extra force and stability. In FIG. 3, none of the digits is locked, which may lead to the same difficulties as described above; namely, that the unlocked digits may get in the way or block a view of the object. In FIG. 4, the ring finger 40 and the pinky finger 50 are locked when the hand 10 is in the three-jaw-chuck position, which gives the user a more accurate grip of the object he or she is trying to grasp.

Figure 5:
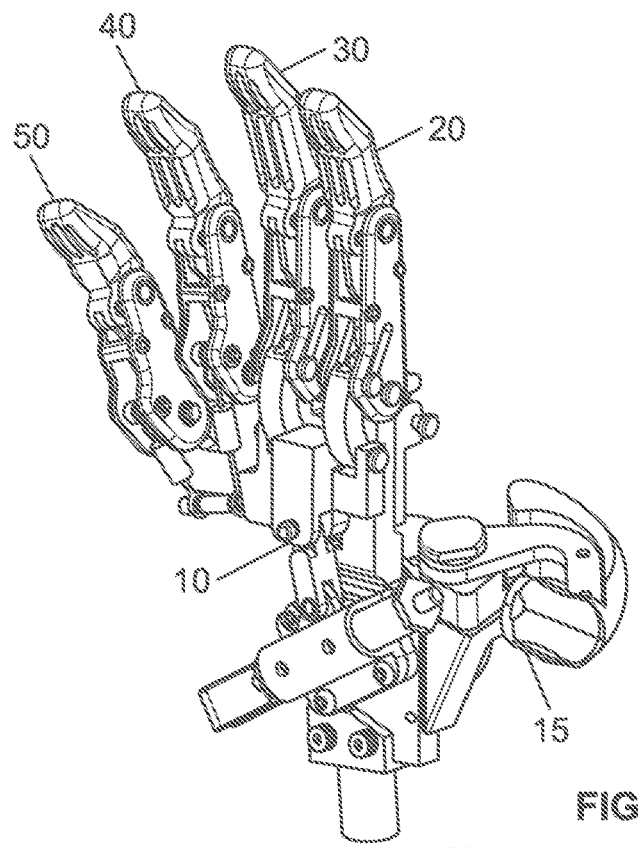
FIG. 5 shows a perspective view of a prosthetic hand arranged in a "palm flat" position.
Figure 6:
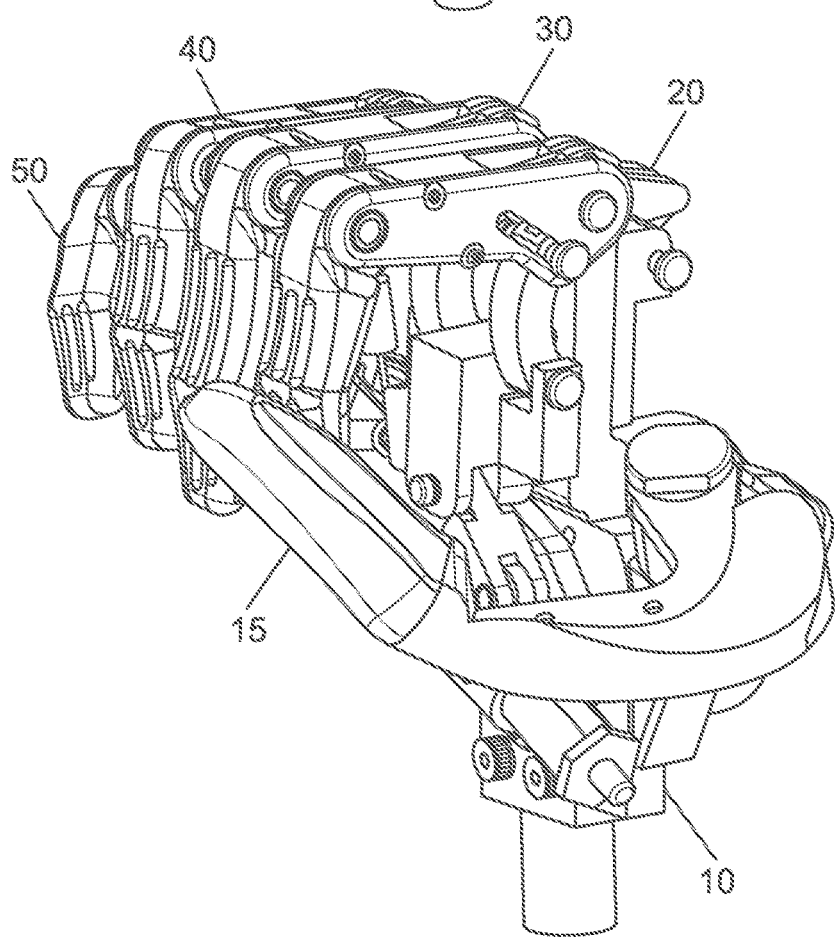
FIG. 6 shows a perspective view of a prosthetic hand arranged in a "cylindrical grasp" position.

In various embodiments, each finger (including the thumb) may be locked in a position of flexion, and unlocked from that position, independently of the other fingers. This allows one or more fingers to be locked while the other fingers are unlocked, as shown in FIGS. 1-4, while also allowing for all fingers to be unlocked (for example, as shown in FIG. 5, where the hand 10 is shown in the "palm flat" position and in FIG. 6, where the hand 10 is shown in the "cylindrical grasp" position).

A lockable finger may be employed on many different kinds of gripping devices, such as prosthetic hands. At least one lockable finger may be used in a gripping device, such as a prosthetic hand, that operates in a voluntary-close ("VC") mode or a voluntary-open ("VO") mode. At least one lockable finger may be used in a gripping device, such as a prosthetic hand, that operates in both a VC mode and a VO mode, for instance by switching between the VC mode and the VO mode. Embodiments of a VO/VC device are described in further detail in U.S. patent application Ser. No. 14/030,095 to J. Sensinger, titled Gripping device with Switchable Opening Modes, for instance, which is incorporated by reference. Additionally, a lockable finger may be employed on myoelectric prosthetic hands, where electrical signals generated by the user are used to help control the myoelectric prosthetic hand. Embodiments of a myoelectric prosthetic hand are described in further detail in U.S. patent application Ser. No. 14/614,256 to J. Sensinger and J. Lipsey, titled Modular and Lightweight Myoelectric Prosthesis Components and Related Methods, for instance, which is incorporated by reference.

Figure 7:
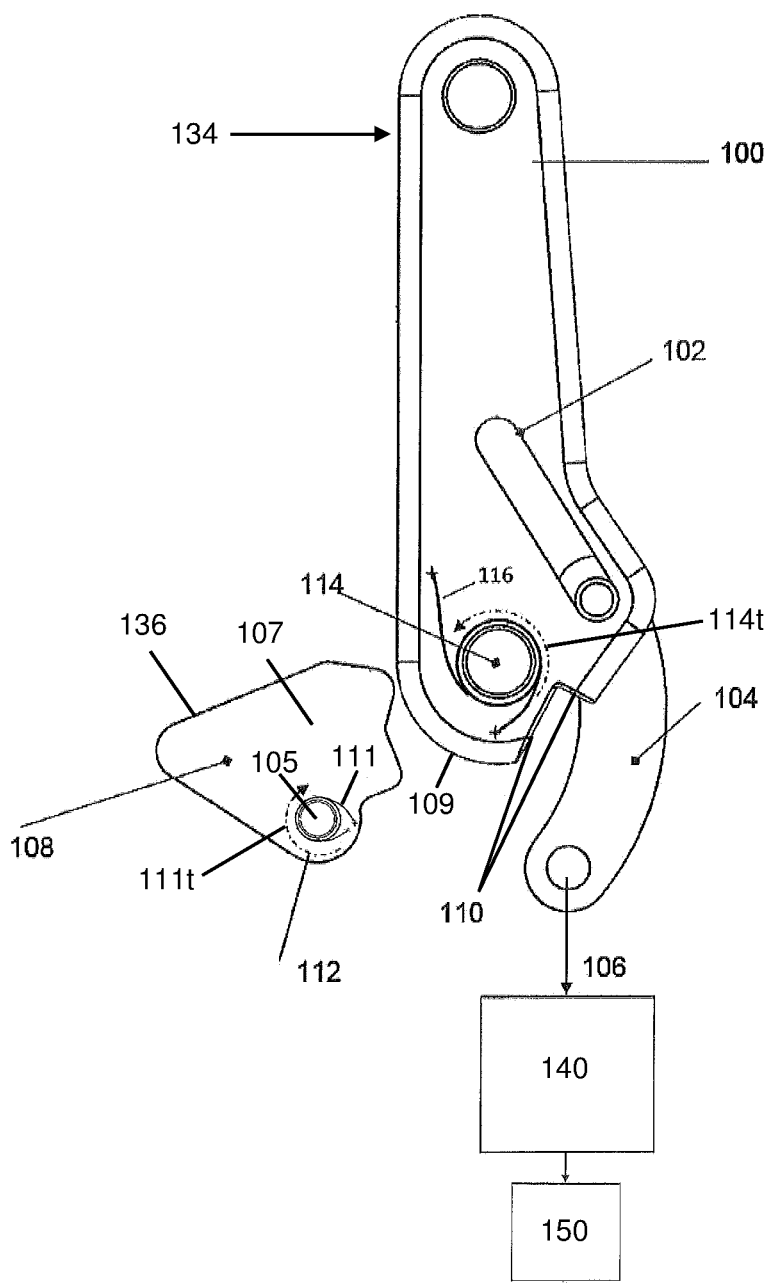
FIG. 7 shows a side view of one embodiment of a lockable finger.

FIG. 7 displays a side view of one embodiment of a lockable finger. As shown in FIG. 7, finger 100 is positioned adjacent to the latch 108. The finger 100 may have a surface 109 and notch sides 110. As shown in FIG. 7, the surface 109 may be rounded. The finger 100 may be configured to receive a locking force 134 from an external source. The locking force 134 may be provided by the user, for instance, by pushing on the finger 100 using his or her other hand, by pushing the finger 100 against an object (such as a wall, a table, or some other object in the user's environment). The locking force 134 may also be provided by other means, such as by another person, or by some other method.

A latch 108 may be positioned adjacent to the proximal finger linkage 100. In one embodiment, the latch 108 may comprise a spring-loaded cam. The latch 108 pivots about a pivot 112. In one embodiment, a spring 111 may provide a torque on the latch 108 in the clockwise direction indicated by arrow 111$t$ and a spring 116 may provide a torque on the finger 100 in the counterclockwise direction indicated by arrow 114$t$. When a locking force 134 is applied to the finger 100, the finger 100 engages with the latch 108 to lock the finger 100 in a position of flexion. The force bias introduced by the spring 116 also prevents the finger 100 from flexing or extending independently of actuation, but it may be overpowered by the locking force 134. In the embodiment shown in FIG. 7, when the locking force 134 is applied to the finger 100, if the torque provided by the locking force 134 is greater the torque 114$t$, the finger 100 begins to rotate about pivot 114. (Spring 116 and the other springs displayed in the figures with a dashed lines may be torsion springs or representations of other springs known in the art.)

As the finger 100 rotates about the pivot 114, the surface 109 comes into contact with a portion 107 of the latch 108. In one embodiment, the portion 107 may protrude from the latch 108. When the surface 109 comes into contact with the portion 107, the surface 109 may push the portion 107 in a direction that causes the rotation of the latch 108 about the latch pivot 105. As the locking force 134 continues to be applied to the finger 100, the finger 100 continues to rotate in a clockwise direction around pivot 114 until the surface 109 no longer is in contact with the latch 108. Once the surface 109 is no longer in contact with the latch 108, a spring 112 may cause the latch 108 to rotate in a clockwise direction, such that the portion 107 or another portion of the latch 108 moves to a position underneath the finger 100. When the finger 100 is sufficiently flexed by the locking force 134 so that it is in a position of full flexion (defined below), the latch 108 and the finger 100 have become positioned with respect to each other so that it the latch 108 is positioned underneath the notch sides 110 of the finger 100. When the locking force 134 is no longer applied, the spring 116 causes the finger 100 to rotate counterclockwise around pivot 114 to return to extension. However, the notch sides 110 press against the latch 108, therefore preventing the finger 100 from extending. In this way, the latch 108 serves as a stopping element, and in the embodiment shown in FIG. 7, the engagement of the finger 100 with latch 108 locks the finger 100 in a position of flexion.

In the embodiment shown in FIG. 7, the latch 108 may be disengaged manually from the finger 100. For instance, the latch 108 may be disengaged by pressing an unlock mechanism 136 that is coupled to the latch 108. The unlock mechanism 136 may push against the latch 108, causing the latch 108 to rotate away from the finger 100, such that the latch 108 is no longer positioned underneath the notch sides 110 of the finger 100. In one embodiment, the unlock mechanism may be a protruding portion of the latch itself. In another embodiment, the unlock mechanism 136 may comprise a bias spring (not shown) that disengages the latch 108 from the finger 100. In one embodiment, the bias spring may be balanced against the torsion spring on the latch. As the unlock mechanism 136 is not under high stress, it can be miniaturized.

Once the latch 108 is disengaged from the finger 100, the spring 116 actuates the finger 100 to a position that allows it to be actuated by the power source 150. In a hand where the default position of the finger 100 is one of extension (in other words, a "voluntary-close" hand), the spring 116 returns the finger 100 to a default extended position. In a hand where the default position of the finger 100 is one of flexion (in other words, a "voluntary-open" hand), the finger 100 is released from the locked position by spring 116 but remains in a semi-flexed position. The spring 116 biases the finger 100 towards extension so as to maintain the position of the actuator linkage 104 at the bottom of the actuator slot 102.

In an embodiment, the finger 100 may be configured so that it can remain in a locked position while at least one other finger on the same hand is free to move. This feature may be important to the user, for instance, if the finger 100 and the at least one other finger are actuated or otherwise moved using the a common linkage. In this embodiment, having one locked finger does not prevent the other one or more fingers from actuating freely. This feature may also be important for the user to move the finger 100 out of the way during an activity that does not require use of the finger 100, such as activities involving trigger grip, fine pinch, or 3-jaw-chuck. This feature may also be important for the user if the user desires to lock the finger 100 to assist with a particular type of grasp. For example, the thumb may be locked to assist with the user grasping an object. Alternately, the thumb may be locked to move it out of the way for activities that do not require the thumb.

For instance, as shown in FIG. 7, an actuator slot 102 is provided in the finger 100 and is configured to receive an actuator linkage 104. The actuator linkage 104 may be coupled to a common link 140 which in turn may be coupled to a power source 150. The arrow 106 in FIG. 7 indicates the direction of the actuation force that the power source 150 provides to the actuator linkage 104 through the common link 140. The power source 150 may be an externally powered motor, a Bowden cable attached to the user's body, or another powered mechanism.

One embodiment achieves movement of unlocked fingers through the use of a slot in the proximal finger linkage at the attachment point of the actuator linkage. Forces on the proximal finger linkage only occur when the actuator linkage is at the end of the slot, ensuring larger surface areas and thus acceptable material pressures. Locking one or more fingers does not interfere with movement of the other fingers in either VO or VC modes, since the actuator link is free to move throughout the range of motion of the slot. Similarly, locking the fingers does not interfere in any way with the ability of the user to obtain proprioceptive input during use of the device, since the actuator link still moves throughout the entire range of motion and is not impeded in any way. As shown in FIG. 7, an actuation slot 102 in the actuation path enables the digit to move through its range of motion to a flexed position without inhibiting the actuator. Manually flexing the finger to a lockable position allows latch 108 to engage with the notch 110 on the proximal finger linkage 100. Latch 108 is biased by a spring 112 to close so that once the digit reaches the locked position, latch 108 will automatically engage with notch 110 and statically lock the digit in a flexed position.

Figure 8:
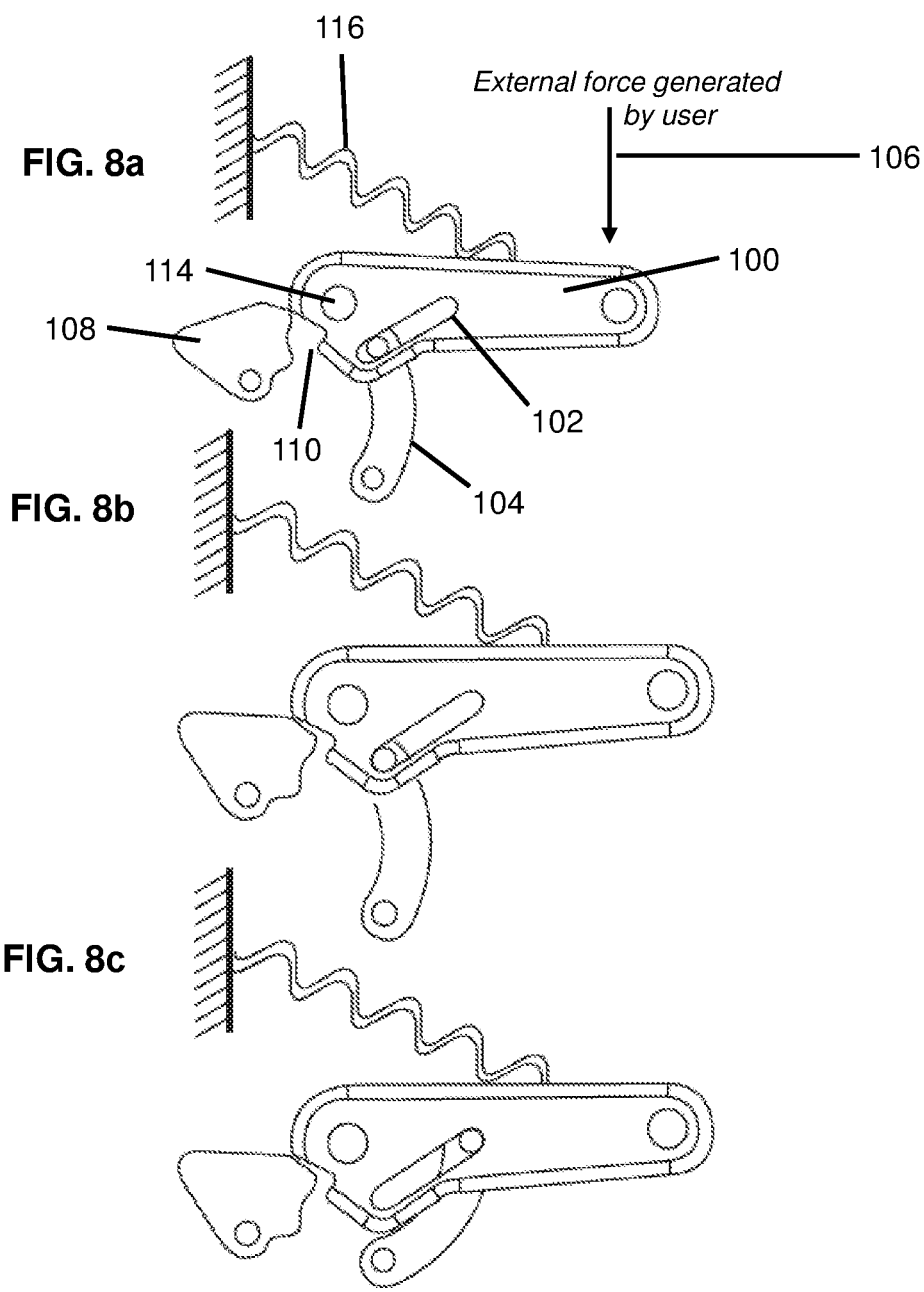
FIGS. 8a, 8b, and 8c show three different configurations of the lockable finger shown in FIG. 7.

FIGS. 8a, 8b, and 8c shows three different representations of the finger 100. Each representation shows the finger 100 in a different configuration during a different stage of use. (It should be noted that in FIGS. 8a, 8b, and 8c, spring 116 is represented as a spring attached to a wall, rather than as a torsion spring as shown in FIG. 7, so that the force it provides on the finger 100 can be more easily visually compared to the locking force 134.)

FIG. 8a shows the finger 100 actuated to the maximum extent of the possible range of the motion of flexion. This position is known as "full flexion." In a preferred embodiment, full flexion occurs at a greater range of motion than can be actuated by the power source 150. This prevents the power source 150 from accidentally locking the digit. In an embodiment, the finger 100 may be configured to reach full flexion just beyond the point necessary for it to engage with the latch 108. In order for full flexion to occur at a greater range of motion than can be actuated by the power source 150, the finger 100 may be constructed so that it can flex beyond the functional range of movement. For instance, if 90 degree flexion is required to accomplish most activities of daily living, the finger 100 may be constructed so that it can flex up to 110 degrees. In this way, the power source 150 is limited to flexing the finger 100 to 90 degrees and then may reach a hard stop. At this point, the user can still manually flex the finger to 110 degrees of flexion, at which point the finger locks. Note that the actuator linkage 104 is not bottomed out in the slot 102. In this embodiment, it indicates that in order to engage the latch 108, the finger 100 must be flexed beyond the capabilities of the power source 150. For the power source 150 to be moving the finger 100 into flexion, the actuator linkage 104 must be bottomed out in the slot 102. However, since the actuator linkage 104 is not in the bottom of the slot 102, FIG. 8a is showing the finger 100 being flexed manually beyond the capabilities of the power source 150.

FIG. 8b shows the finger 100 locked in a position of flexion. Once the finger 100 has been pushed into the position of full flexion, the latch 108 flips into place, engaging with the notch sides 110 to prevent extension of the finger 100. This position can be accomplished by the locking force 134, rather than by the actuator force 106.

FIG. 8c shows the finger 100 locked in a position of flexion, with the actuator linkage 104 free to move throughout its normal range of motion in the actuation slot 102 in the proximal digit linkage 100. Locking of the finger 100 does not prevent the at least one other finger (including a thumb) from being actuated through common link 140 and power source 150.

Figure 9:
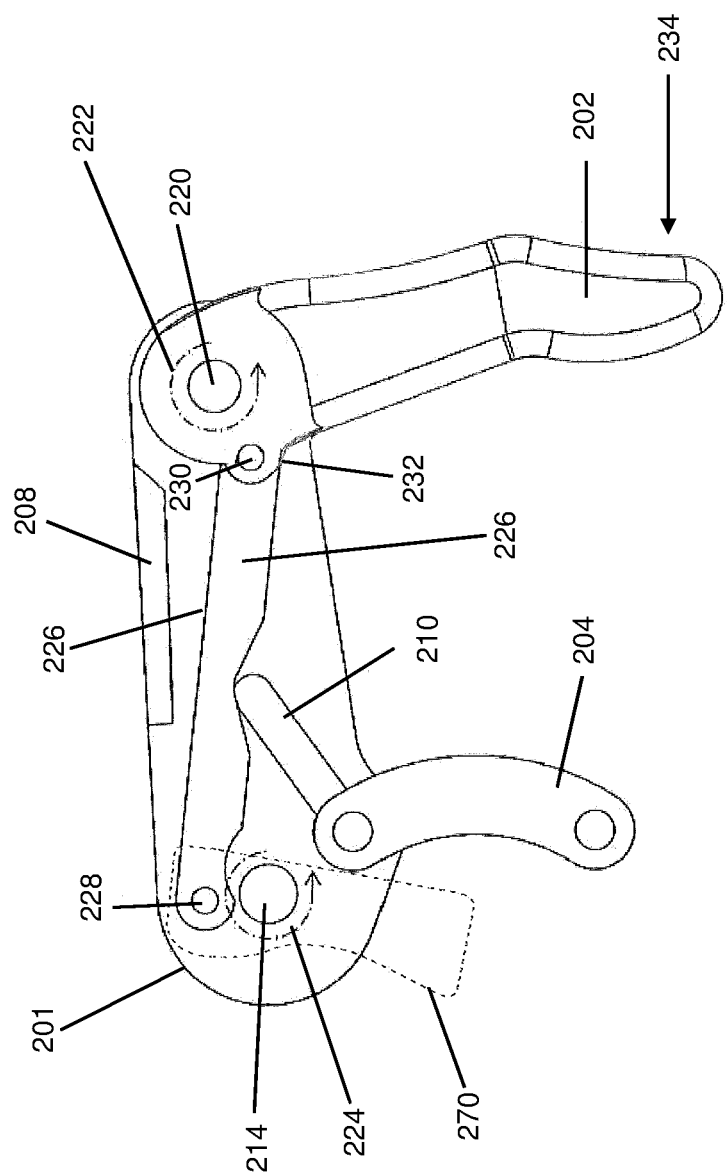
FIG. 9 shows a second embodiment of a lockable finger.

In another embodiment, a four-bar linkage may be inserted into the fingers, in order to kinematically couple PIP flexion to MCP flexion. In this manner the fingers remain relatively flat during palm-flat, yet achieve the required PIP flexion angle for chuck-grasp. The four-bar linkage maximizes pinch force while still achieving a kinematically acceptable motion profile, within the constraints of an anthropomorphic hand envelope. Another embodiment of a locking finger is shown in FIG. 9. The finger 200 may have a proximal phalanx 201 and a distal phalanx 202. (A "phalanx" is the part of the finger between two joints, while "proximal" and "distal" are used to describe the relative positions of the phalanxes to the body, with the "proximal" phalanx closer to the body and the "distal" phalanx further from the body.) As shown in FIG. 9, in one embodiment, an upper portion of the distal phalanx 202 may be configured in a cam shape, so that a portion 232 of the distal phalanx 202 extends from the surface of the distal phalanx 202 and allows for the receipt of a pin 230 that connects the distal phalanx 202 to the locking linkage 226. In one embodiment, a support member 270 may be provided that connects to the proximal phalanx 201 by MCP joint 214 and connects to the locking linkage 226 by pin 228. (MCP joint 214 may be a pin or other suitable fastening mechanism.) Pin 230, positioned as shown in FIG. 9 to the left of the PIP joint 220, may connect the other end of the locking linkage 226 to the distal phalanx 202. It should be understood that while pins may used to connect different components of the finger, as shown in the various figures herein, other fastening mechanisms known in the art may be used instead. A slot 210 and actuator linkage 204 may be provided, for the finger 200 to be flexed and/or extended independently of other fingers.

In one embodiment, the user pushes on the distal phalanx 202 to lock the finger 200. The finger 200 may lock due to engagement between the locking linkage 226 and the stopping element 208. In one embodiment, the stopping element 208 may be located on the proximal phalanx 201.

The locking force 234 applied to the distal phalanx 202 causes the distal phalanx 202 to rotate about PIP joint 220. As shown in FIG. 9, the distal phalanx 202 begins to rotate in a clockwise direction about joint 220, and continues to rotate until the locking linkage 226 pushes against the stopping element 208. In doing so, the distal phalanx 202 is flexed beyond the full flexion provided by the actuator. Additionally, the locking linkage 226 passes through the singularity defined by the pin 228, pin 230, and PIP joint 220 being collinear. Once the locking linkage 226 passes through this singularity, the finger 200 remains locked (as described in further detail below). FIGS. 10a, 10b, and 10c show side views of the stages of the finger 200 as it is locked in a position of flexion.

A more detailed description of a "singularity" may be found in U.S. patent application Ser. No. 14/030,095 to J. Sensinger, titled Gripping device with Switchable Opening Modes. Briefly, a mechanical singularity is when the position or configuration of the mechanism and its subsequent behavior cannot be predicted. With respect to finger 200, when the pin 228, pin 230, and PIP joint 220 are aligned, it is not possible to determine whether pin 230 will rotate about PIP joint 220 in a clockwise direction (and so working to flex the finger 200) or in a counterclockwise direction (and so working to extend the finger 200).

Figure 11:
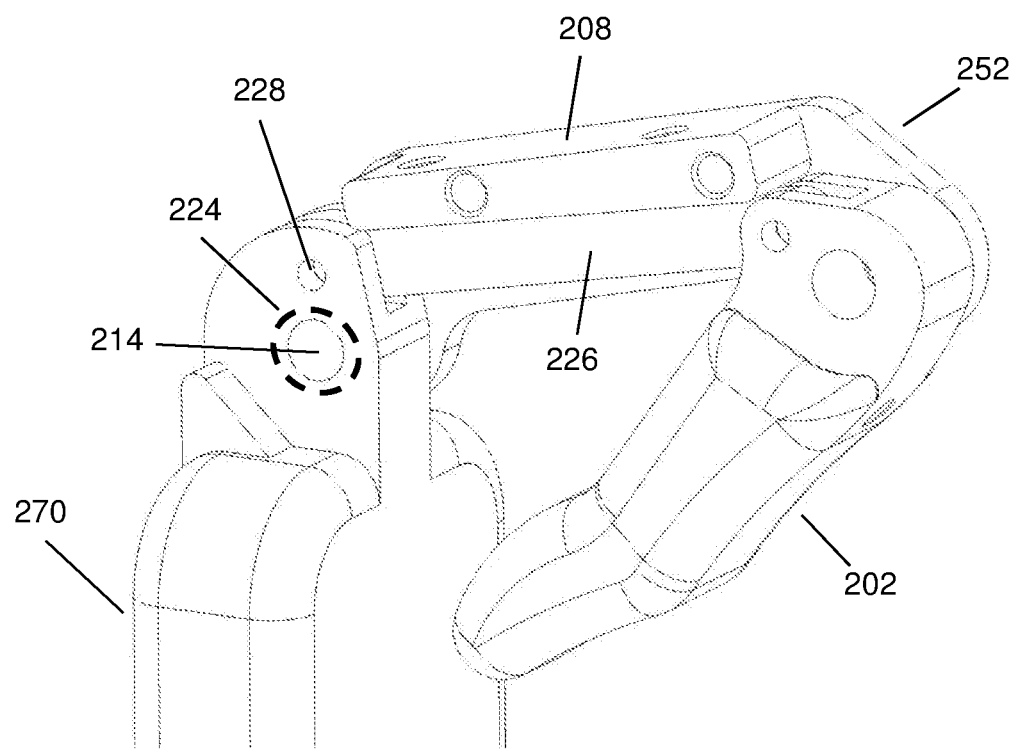
FIG. 11 shows a perspective view of the lockable finger shown in FIG. 9.

FIG. 11 shows a perspective view of the finger 200 locked in a position of flexion, where the locking linkage 226 is prevented from further flexion by stopping element 208. FIG. 11 also shows wall 252, which provides common support as shown for the components of the finger 200. Another wall on the opposite side of the stopping element 208 and locking linkage 226 may be provided, but is omitted from FIG. 11 so that the reader can better see the internal arrangement of the finger 200.

In one embodiment, at least one passive spring provides a torque that keeps the finger in a locked position. In one embodiment, shown in FIG. 11, spring 224 provides a torque in a counterclockwise direction. When the finger 200 is locked, the torque from spring 224 attempts to extend the proximal phalanx 201. However, as the proximal phalanx 201 rotates towards extension, the locking linkage 226 creates a clockwise rotation about pin 230, due to the fixed radius of pin 230 from PIP joint 220. This clockwise rotation of the distal phalanx 202 moves the locking linkage 226 towards extension, where it collides with the stopping element 208. In order for the finger 200 to continue into extension, the locking linkage 226 would need to occupy the space of the stopping element 208. However, since the stopping element 208 is present, the spring 224 at the MCP joint 214 acts to continuously engage the locking linkage 226 and the stopping element 208. This continued engagement of the locking linkage 226 with the stopping element 208 keeps the finger 200 locked in the position of flexion.

FIGS. 12a, 12b, and 12c display three side views of the finger 200 being unlocked. In FIG. 12a, a force 260 may be applied to a top surface of the proximal phalanx 201. The force 260 may be applied by the user's other hand, or by an object in the user's environment. The force 260 causes the finger 200 to flex. In one embodiment, the force 260 causes the proximal phalanx 201 to rotate in a clockwise direction, which rotates the locking linkage 226 to the singularity. FIG. 12b shows the locking linkage 226 at the point of singularity, at which point the PIP spring 222 pulls the distal phalanx 202 outward and MCP spring 224 pushes the proximal phalanx 201 towards extension. The springs 222 and 224 therefore work together, in the directions indicated by the arrows shown around the MCP joint 114 and the PIP joint 120, respectively, to push the finger 200 back into the unlocked position shown in FIG. 12c.

Figure 13A:
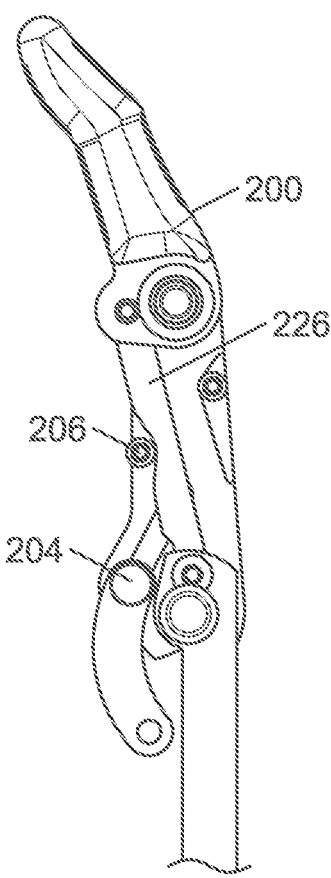
FIGS. 13a and 13b show one embodiment of a lockable finger with a contoured linkage.
Figure 13B:
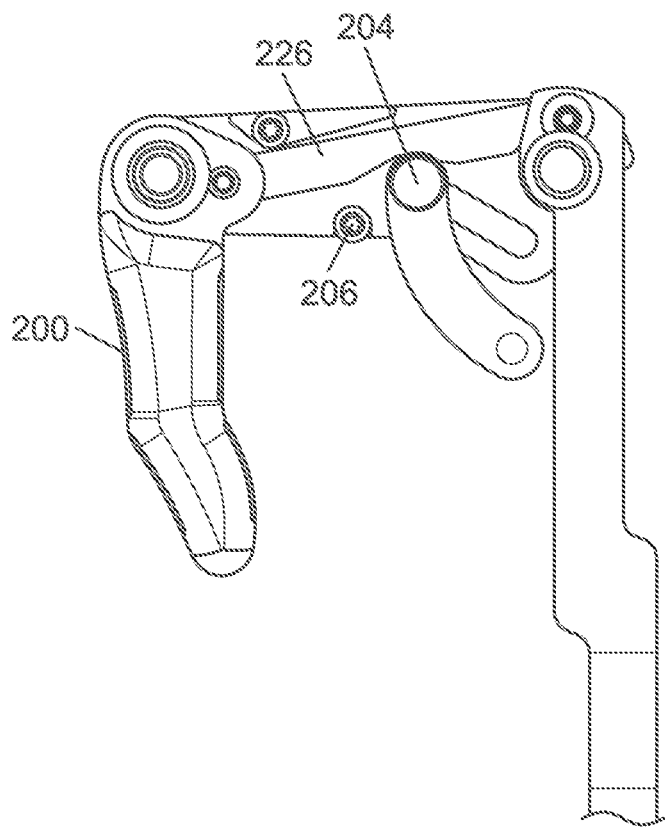

In an embodiment of the finger, the locking portion may physically configured to avoid catching or otherwise interfering with other portions of the system. For example, as shown in FIGS. 13a and 13b, the locking linkage 226 may be contoured so that its movement between extension and flexion of the finger 200 does not interfere with the actuator linkage 204 or the support member 206. Equivalent support members are shown in the profile views FIGS. 14-16. As shown in FIG. 13a, the locking linkage 226 is contoured to receive support member 206 when the finger 200 is extended. As shown in FIG. 13b, the same contour of the locking linkage receives the actuator linkage 204 when the finger 200 is extended.

In alternative embodiments, a four-bar mechanism is used in each finger, and a fifth bar in each finger is used to transmit torque from the body-powered mechanism, such as a Bowden cable, to the finger. These fifth bars may be rigidly linked across the fingers, and connected by some method to a VO/VC switch mechanism, allowing the hand to function either as a VO or a VC hand. Each of the actuator links is attached to the output of the VO/VC mechanism, such that the output of the VO/VC mechanism is a linkage. The actuator links are attached through a linear bushing to ensure that each of the fingers moves at the same rate. The VO/VC mechanism is in turn attached to the Bowden cable or external motor, which provides the input to the VO/VC mechanism.

Figure 14:
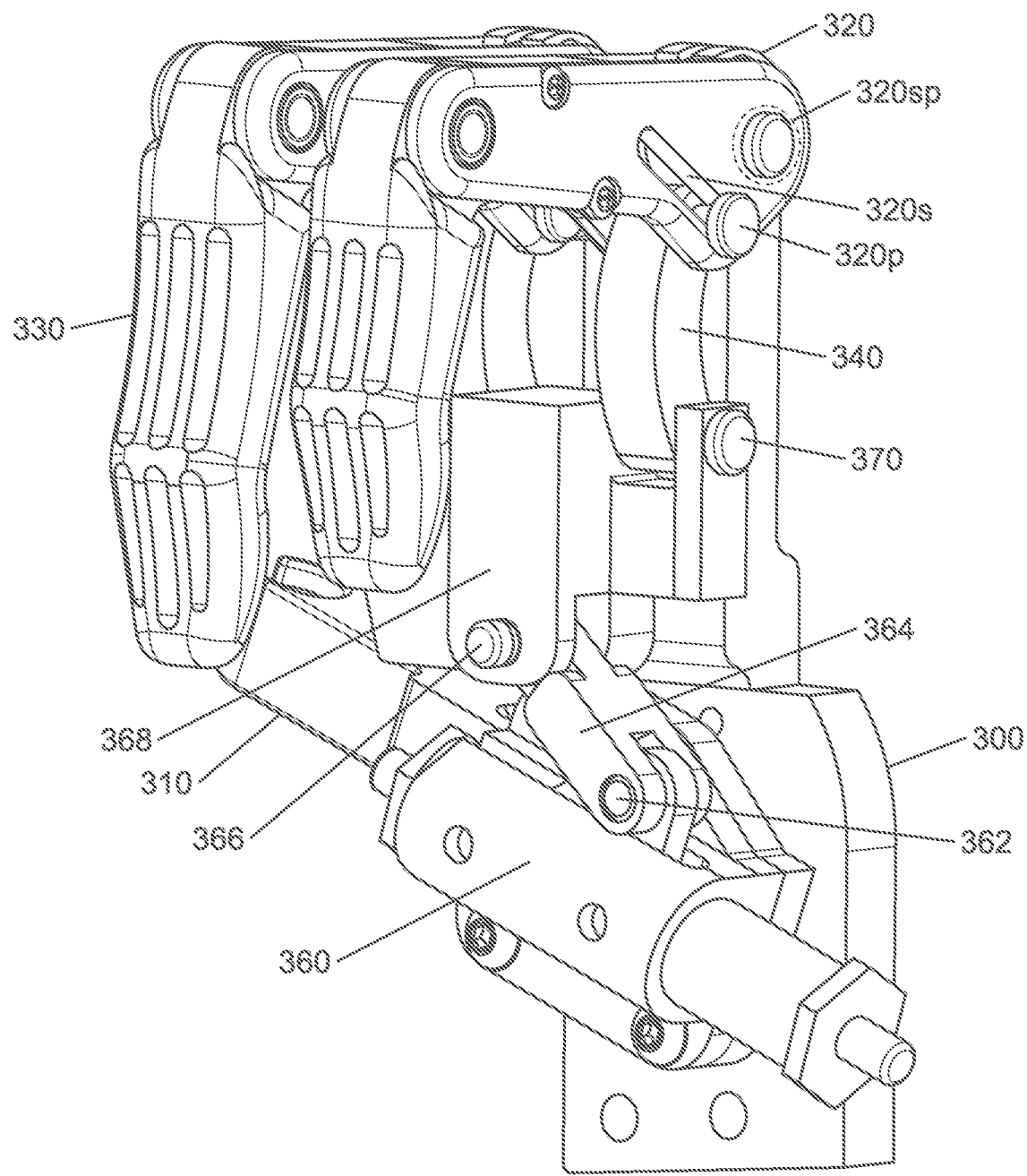
FIGS. 14 and 15 show one embodiment of a lockable finger in use with a hand, where the hand is configured to operate in voluntary-open (VO) mode.
Figure 15:
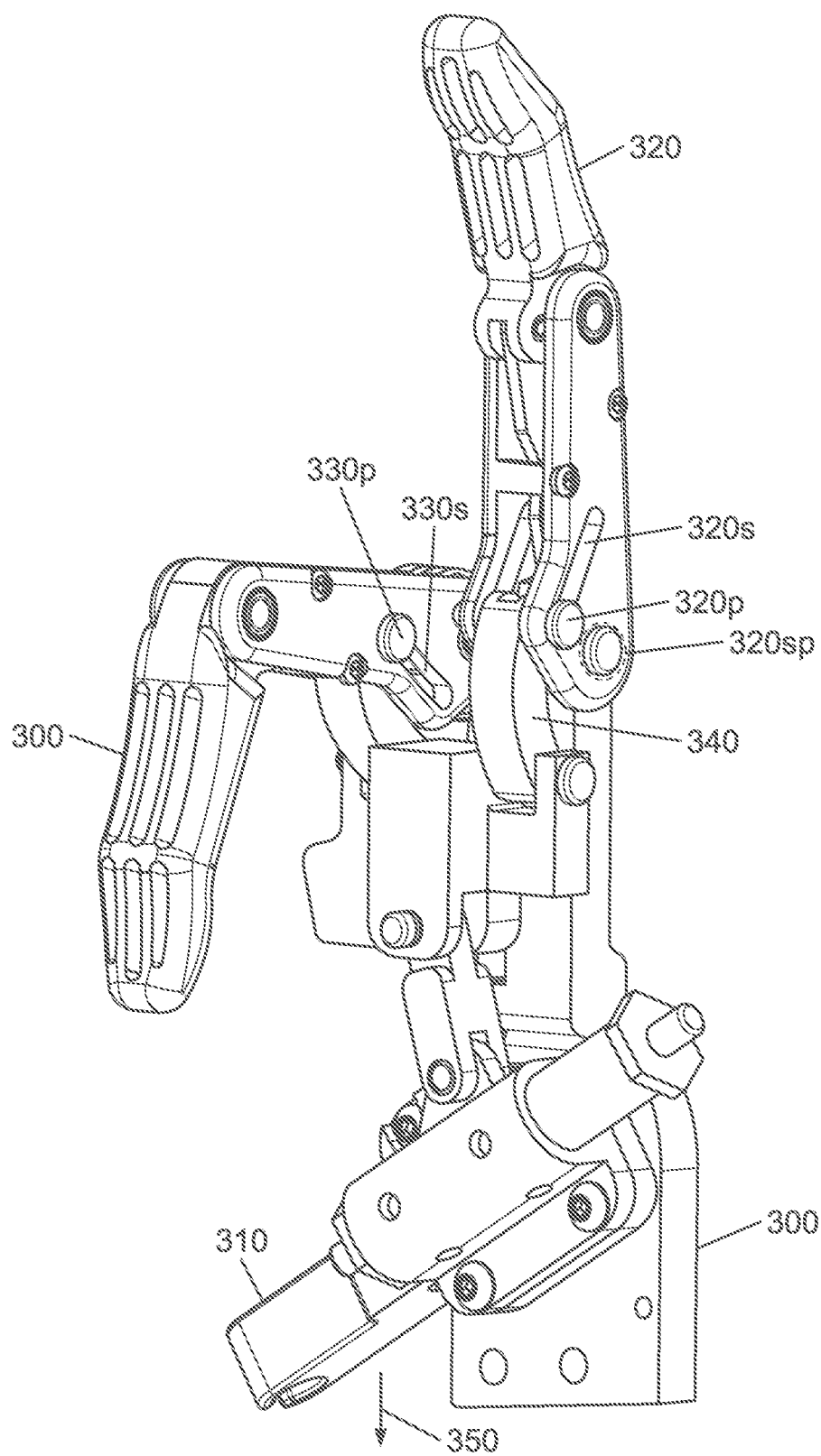

FIGS. 14 and 15 show embodiments of a locking finger in use with a hand 300, where the hand 300 is configured to operate in voluntary-open (VO) mode. In FIG. 14, the hand 300 is shown coupled to an actuation lever 310. Finger 320 and finger 330 each have a slot 320s and 330s, respectively. In the embodiment shown in FIG. 14, the actuation lever 310 is coupled to the fingers 320 and 330 by a transmission. Actuation of the actuation lever 310 causes rotation of the actuation lever 310 about a central pivot, causing switch 360 to rotate in a counter clockwise direction. In doing so, switch 360 acts on pin 362 and link 364 to transfer an upward force through pin 366 to the coupler linkage 368. The coupler linkage 368 is connected by pin 370 to driver linkages 340, which actuate the fingers 320 and 330. The driver linkage 340 is coupled to finger 320 by a pin 320p and is coupled to finger 330 by a pin 330p. Pin 320p is positioned in the slot 320s and pin 330p is positioned in the slot 330s. As the driver linkage 340 moves in the upward direction, each pin 320p and 330p allows its respective finger 320 and 330 to move by releasing it from VO mode and allowing it to extend. In one embodiment, extension may be provided by one or more springs coupled to each finger.

However, a finger, for example finger 330, may be locked, so that actuation of the actuation lever 310 does not cause the finger to extend. For example, FIG. 15 shows finger 330 locked in a position of flexion even as the actuation lever 310 has been actuated by a force 350, such as being pulled on by a Bowden cable. As the hand 300 is actuated, the driver linkage 340 moves in an upward direction. Spring 320sp pulls finger 320 into a position of extension. Finger 330 has a similar spring around its joint, but because the finger 330 is locked, instead of that spring acting on finger 330 to cause extension, pin 330s instead slides through slot 330p, and comes to rest at the top of slot 330p as shown in FIG. 15.

Figure 16:
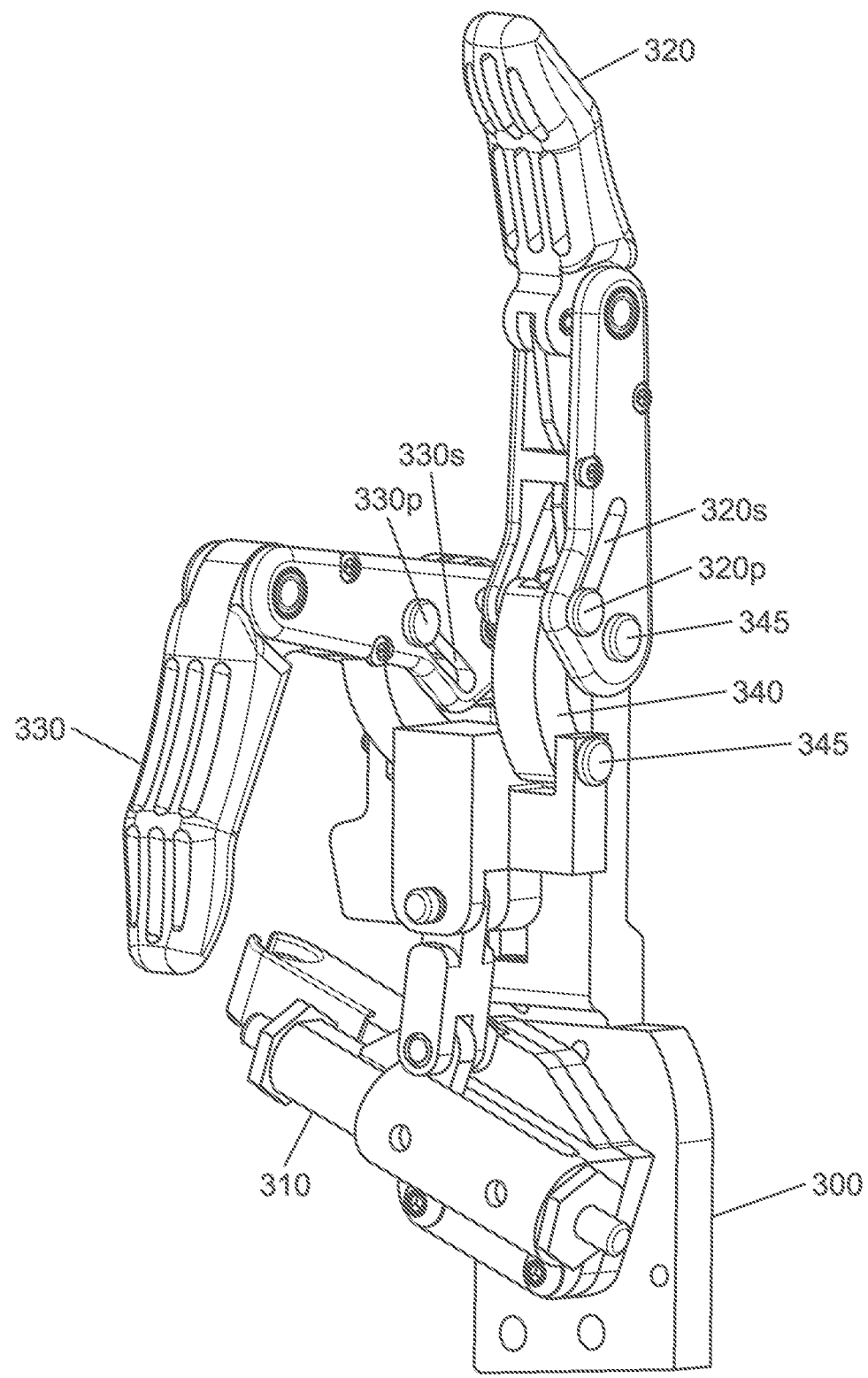
FIGS. 16 and 17 show one embodiment of a lockable finger in use with a hand, where the hand is configured to operate in a voluntary-close (VC) mode.
Figure 17:
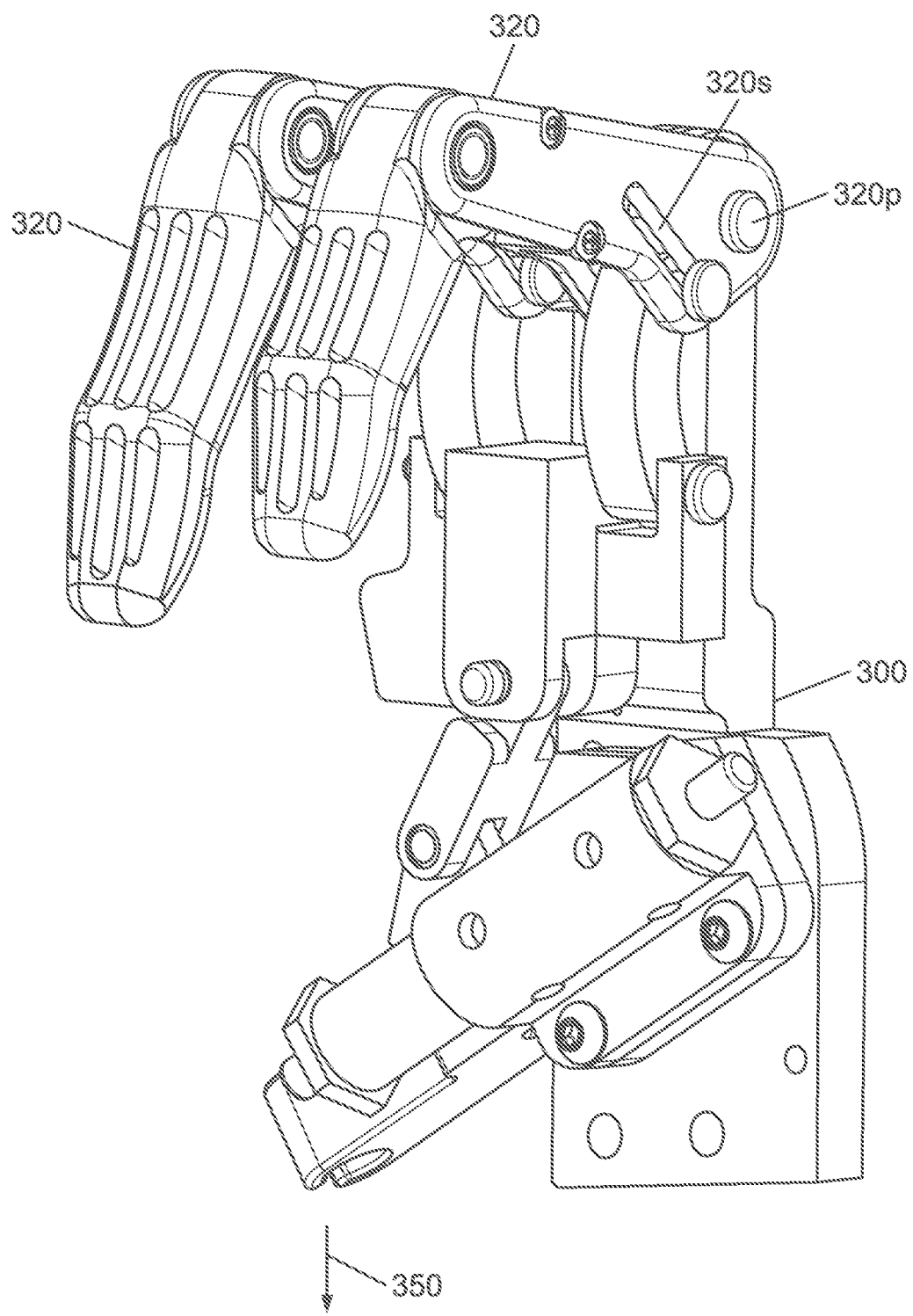

FIGS. 16 and 17 show an embodiment of a locking finger in use with a hand 300, where the hand is configured to operate in a voluntary-close (VC) mode. As shown in FIG.

16, the finger 330 is locked in a position of flexion, and the pin 330p is at the top of the slot 330s. The finger 320 is in a position of extension due to torque provided by a spring about main pivot 345. In FIG. 17, with the hand 300 in VC mode, a force 350 is applied to flex the finger 320. The pin 320p moves to the bottom of slot 320s to flex the finger 320, while the pin 330p slides through the bottom of the slot 330s as the finger 330 is already locked in a position of flexion.

What is claimed:

1. A prosthetic device comprising:
  a first prosthetic digit and a second prosthetic digit, wherein each prosthetic digit comprises:
    i. a first phalange comprising a proximal end and a distal end;
    ii. a proximal interphalangeal (PIP) joint;
    iii. a second phalange coupled to the distal end of the first phalange at the PIP joint, a portion of the second phalange that is coupled to the first phalange comprising a cam;
    iv. a metacarpophalangeal (MCP) joint;
    v. a four-bar linkage configured to operatively couple the PIP joint to the MCP joint, the four-bar linkage comprising a locking linkage extending along the first phalange, wherein the proximal end of the first phalange receives a first pin that connects the proximal end to the locking linkage, and the distal end of the first phalange receives a second pin that connects the cam of the second phalange to the locking linkage; and
  a stopping portion comprising a stopping element configured to be positioned above the locking linkage, wherein, in response to a force applied to move the second phalange into a position of flexion, the cam of the second phalange rotates in a first direction about the PIP joint until the locking linkage encounters the stopping element such that the second phalange is in a position of flexion and the locking linkage passes through a mechanical singularity, defined by the first pin, the second pin, and the PIP joint being collinear, to lock the prosthetic digit into the position of flexion.

2. The prosthetic device according to claim 1, wherein the stopping portion of each prosthetic digit is positioned on the first phalange of the prosthetic digit.

3. The prosthetic device according to claim 1, further comprising:
  an actuator linkage coupled to each of the first prosthetic digits;
  wherein the actuator linkage is configured to extend the first prosthetic digit when the first prosthetic digit is not locked in a position of flexion; and
  wherein the actuator linkage is configured to extend the second prosthetic digit when the second prosthetic digit is not locked in a position of flexion.

4. The prosthetic device according to claim 3, further comprising:
  a third prosthetic digit and a fourth prosthetic digit;
  wherein the first prosthetic digit, second prosthetic digit, third prosthetic digit, and fourth prosthetic digit comprise prosthetic fingers.

5. The prosthetic device according to claim 1, wherein the PIP joint comprises a spring configured to bias the second phalange into an open position when the second pin and the cam are on a first side of the mechanical singularity and bias the second phalange into the position of flexion when the second pin and the cam are on a second side of the mechanical singularity.

6. The prosthetic device according to claim 1, wherein the locking linkage of each prosthetic digit moves independently of the other locking linkages such that each prosthetic digit can be in a locked position or an unlocked position, independently of the other prosthetic digits.

* * * * *